United States Patent [19]

Driver et al.

[11] Patent Number: 5,100,876
[45] Date of Patent: Mar. 31, 1992

[54] 16-DECARBOXY-16-HYDROXY DERIVATIVES OF AMPHOTERICIN B

[75] Inventors: Michael J. Driver; William S. MacLachlan; Andrew W. Taylor, all of Epson, England

[73] Assignee: Beecham Group p.l.c., Middlesex, England

[21] Appl. No.: 448,551

[22] Filed: Dec. 11, 1989

[30] Foreign Application Priority Data

Dec. 19, 1988 [GB] United Kingdom ............... 8829593

[51] Int. Cl.$^5$ .................... A61K 31/70; C07H 17/08
[52] U.S. Cl. .................................. 514/31; 536/6.5
[58] Field of Search .............. 536/6.5, 18.5; 514/31

[56] References Cited

U.S. PATENT DOCUMENTS 4,223,130 9/1980 Weinstein ........................ 536/6.5
4,235,993 11/1980 Sipos et al. ..................... 536/6.5

OTHER PUBLICATIONS

Nicolau et al., J. Am. Chem. Soc. 1988, 110, 4660–4672, "Chemistry of Amphotericin B".
Nicolau et al., J. Am. Chem. Soc. 1988 110, 4696–4705, "Total Synthesis of Ampletricin B".
Cram et al., Organic Chemistry, 2nd ed. (1964) p. 556.

Primary Examiner—Johnnie R. Brown
Assistant Examiner—Elli Peselev
Attorney, Agent, or Firm—Hopgood, Calimafde, Kalil, Blaustein & Judlowe

[57] ABSTRACT

Compounds of the formula (I), or pharmaceutically acceptable salts thereof:

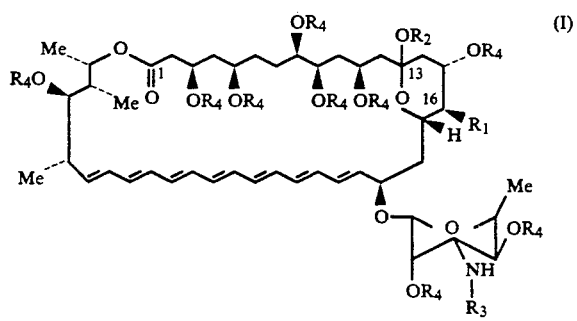

wherein $R_1$ is —$CH_2OH$; $R_2$ is hydrogen or $C_{1-8}$ alkyl; $R_3$ is hydrogen or an amine protection group; and each $R_4$ is hydrogen; their preparation, compositions containing them and their use in the treatment of fungal infections are described.

6 Claims, No Drawings

16-DECARBOXY-16-HYDROXY DERIVATIVES OF AMPHOTERICIN B

The present invention relates to novel compounds, their preparation and their use in the treatment of fungal infections in animals, including humans.

The polyene macrolide amphotericin B, produced by *Streptomyces nodosus*, is widely used for the treatment of fungal infections.

Amphotericin B is the only complex polyene macrolide whose molecular structure and absolute configuration have been firmly established by x-ray crystallographic analysis. Amphotericin B has the formula (A):

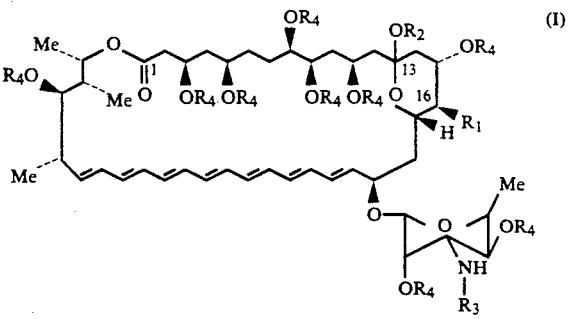

(I)

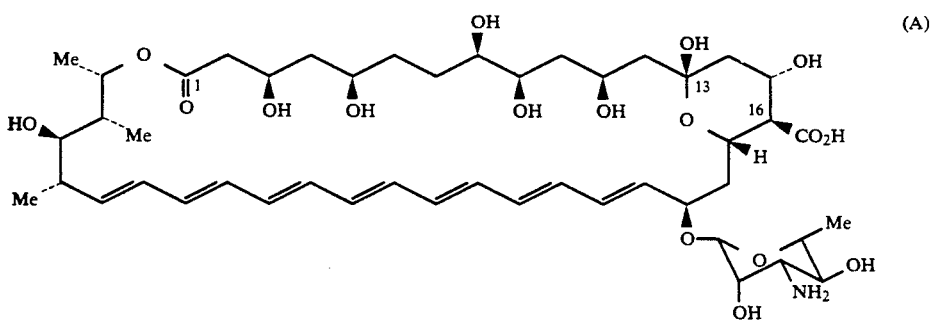

(A)

Derivatives of amphotericin B are reported in the literature. Nicolaou et al. (J. American Chem. Soc., 110, 4660, (1988)) describe the synthesis of a compound of formula (B):

wherein $R_1$ is —$CH_2OH$; $R_2$ is hydrogen or $C_{1-8}$ alkyl; $R_3$ is hydrogen or an amine protection group; and each $R_4$ is hydrogen.

Unless otherwise specified, an alkyl group is prefera-

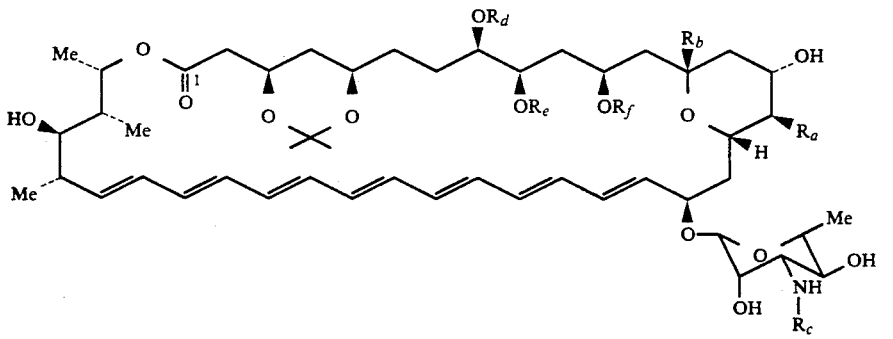

(B)

wherein $R_a$ is —$CH_2OH$, $R_b$ is methoxy, $R_c$ is acetyl, and either $R_d$ is hydrogen and $R_e$ and $R_f$ together are isopropylidene, or $R_d$ and $R_e$ together are isopropylidene and $R_f$ is hydrogen.

No pharmacological activity has been attributed to compounds of formula (B).

Novel derivatives of amphotericin B have now been prepared having a hydroxymethyl group at the 16-position, which derivatives have been shown to have antifungal activity and have potential utility as anti-fungal agents.

Accordingly, the present invention provides a compound of formula (I) or a pharmaceutically acceptable salt thereof:

bly a $C_{1-6}$ alkyl group, more preferably a $C_{1-4}$ alkyl group and may be straight-chain or branched.

The term pharmaceutically acceptable salt encompasses solvates and hydrates. Thus where compounds of formula (I) or pharmaceutically acceptable salts thereof form solvates or hydrates, these also form an aspect of the invention.

The compounds of formula (I) wherein $R_3$ is hydrogen can form acid addition salts with acids, such as conventional pharmaceutically acceptable acids, for example hydrochloric, hydrobromic, phosphoric, acetic, fumaric, salicylic, citric, lactic, mandelic, tartaric, oxalic, methanesulphonic, aspartic and ascorbic. The invention also extends to quaternary salts.

Values for $R_3$ include hydrogen, acetyl, 9-fluorenylmethoxycarbonyl, trichloroethoxycarbonyl, 2-methylsulphonylethoxycarbonyl and 2-trimethylsilylethoxycarbonyl. Preferably $R_3$ is hydrogen, acetyl, or 9-fluorenylmethoxycarbonyl. More preferably $R_3$ is hydrogen.

Also included within the scope of compounds in which $R_3$ is an amine protection group are further amino group derivatives including, acyl derivatives bearing a basic substituent such as N-D-lysyl and N-D-ornithyl derivatives, guanidine derivatives, and N-glycosyl derivatives. The preparation of further amino group derivatives is described in European Patent Publication 0 010 297 (Schering) European Patent Publication 0 031 722 (Dumex) and U.S. Pat. No. 4,195,172.

Preferred values for $R_2$ include hydrogen and methyl.

The present invention also provides a process for the preparation of compounds of formula (I) which process comprises the selective reduction of a compound of formula (II):

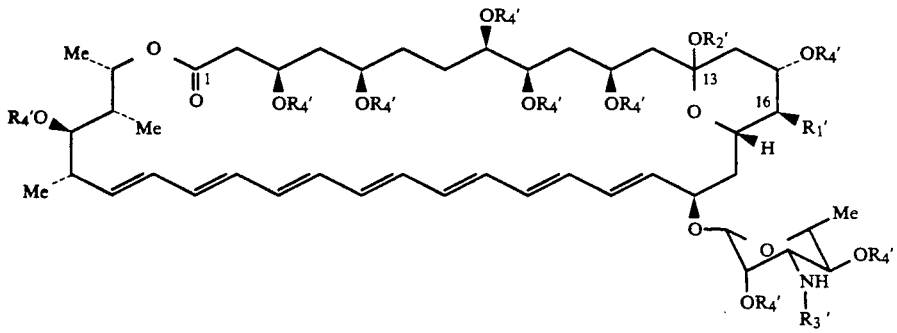

wherein $R_1'$ is an activated carboxylic acid derivative; $R_2'$ is $C_{1-8}$ alkyl; $R_3'$ is an amine protection group; and each $R_4'$ is hydrogen; and thereafter, optionally or as necessary and in any appropriate order converting $R_2'$ to $R_2$, converting $R_3'$ to $R_3$, interconverting $R_2$, interconverting $R_3$, and forming a pharmaceutically acceptable salt.

It will be understood that the term activated carboxylic acid derivative when used herein includes a carboxylic acid group modified by chemical reaction into an activated form amenable to reduction by reaction with a selective reducing agent.

The term activated carboxylic acid derivative includes alkyl, aryl and heteroaryl esters and thioesters, acid halides, acid anhydrides and amides such as N-methyl-N-methoxy amides.

An $R_1'$ carboxylic acid derivative activated for reaction with a selective reducing agent is suitably a $C_{1-6}$ alkyl ester such as methoxycarbonyl or ethoxycarbonyl, or a thioester, preferably a heteroarylthioester such as a pyridylthioester.

Favourably $R_1'$ is methoxycarbonyl or 2-pyridylthiocarbonyl.

Suitable values for $R_2'$ include methyl and ethyl, preferably methyl.

$R_3'$ amine protection groups are chosen such that they are stable to the reduction process utilised for the preparation of compounds of formula (I). Preferably an $R_3'$ amine protection group is readily removable subsequent to the reduction process to provide a compound of formula (I) in which $R_3$ is hydrogen.

Values for $R_3'$ include acetyl, 9-fluorenylmethoxycarbonyl, trichloroethoxycarbonyl, 2-methylsulphonylethoxycarbonyl and 2-trimethylsilylethoxycarbonyl. Favourably $R_3'$ is acetyl or 9-fluorenylmethoxycarbonyl, preferably 9-fluorenylmethoxycarbonyl.

The selective reduction of compounds of formula (II) may be carried out using a borohydride reducing agent such as sodium borohydride or lithium borohydride, preferably sodium borohydride, in a solvent such as methanol or a solvent mixture such as methanoltetrahydrofuran. Efficient reduction is achieved using an excess of the reducing agent, for example from 10 to 30 molar equivalents, at reduced to elevated temperatures, for example ranging from $-30°$ C. to $50°$ C. Preferably the reducing agent is added to a solution of a compound of formula (II) at reduced temperature, for example $0°$ C., and the reaction mixture is then allowed to reach ambient temperature. Reaction times will vary according to reaction conditions and the chosen compound of formula (II). Reaction times may for example vary between 0.1 and 3 hours and more generally between 0.2 and 1 hour.

Where $R_2$ in compounds of formula (I) is hydrogen, conversion of $R_2'$ $C_{1-8}$ alkyl to $R_2$ hydrogen may be carried out under acid-catalysed conditions using water or a mixture of water and tetrahydrofuran as solvent, preferably using a solvent mixture comprising 10–50% water in tetrahydrofuran. A suitable acid catalyst for this reaction is 10-camphorsulphonic acid or pyridinium p-toluenesulphonate. The reaction may be carried out at reduced or elevated temperatures, for example from $-30°$ C. to $50°$ C. and preferably from $0°$ C. to room temperature, over a time period ranging from 0.1 to 5 hours and preferably 0.3 to 2 hours.

Where $R_3$ in compounds of formula (I) is hydrogen, conversion of a readily removable $R_3'$ amine protection group to $R_3$ hydrogen may be carried out under basic conditions.

For example an $R_3'$ amine protection group, such as 9-fluorenylmethoxycarbonyl, may be removed under basic conditions in a solvent such as methanolic dimethyl sulphoxide. Suitable bases for amine deprotection include ammonia, dialkylamines such as dimethylamine and diethylamine, trialkylamines such as triethylamine, cyclic amines and especially cyclic secondary amines such as morpholine, piperazine and more especially piperidine, and diazabicyclic bases such as 1,5-diazabicyclo[4.3.0]non-5-ene (DBN) and preferably 1,8-diazabicyclo[5.4.0]undec-7-ene (DBU).

The amine deprotection may be carried out using from 1–10 equivalents of base, preferably from 1–2 equivalents, at reduced or elevated temperatures, for example from $-30°$ C. to $50°$ C. and preferably from $0°$ C. to room temperature, over a time period ranging from 1 minute to 5 hours and preferably from 30 minutes to 2.5 hours.

Intermediate compounds of formula (II) may be prepared from the natural product amphotericin B by carrying out the following steps in any appropriate order:

(a) activating the 16-position carboxy group, for example by esterification to give an $R_1'$ $C_{1-6}$ alkyl ester or thioester;

(b) selectively exchanging the 13-position anomeric hydroxyl group to give an $R_2'$ $C_{1-8}$ alkyl group; and (c) protecting the amine function of the 19-position sugar moiety with an $R_3'$ amine protection group.

The 16-position carboxyl group may, for example, be converted to an $R_1'$ methoxycarbonyl group using diazomethane in an ether solvent at reduced temperature.

The 13-position anomeric hydroxyl group may be selectively exchanged using the appropriate $C_{1-8}$ alkyl alcohol in the presence of an acid catalyst such as 10-camphorsulphonic acid or pyridinium p-toluenesulphonate under anhydrous conditions. The reaction may be carried out in an inert solvent such as tetrahydrofuran and the alcohol may act either wholly or partially as the solvent. The reaction is conveniently carried out in the presence of an $H_2O$-scavenger such as molecular sieves and/or under an inert atmosphere.

$R_3'$ amine protection groups may be introduced by standard procedures. For example, an $R_3'$ acetyl amine protection group may be introduced by reaction of the primary amine function of the sugar moiety with acetic anhydride in a methanol-dimethyl sulphoxide solvent mixture at reduced temperature, for example at 0° C.

An $R_3'$ 9-fluorenylmethoxycarbonyl amine protection group may be introduced by addition of 9-fluorenylmethyl chloroformate to a solution of the primary amine in methanol-dimethylformamide under anhydrous conditions, in the presence of a base such as potassium carbonate.

Alternatively an $R_3'$ 9-fluorenylmethoxycarbonyl group may be introduced by addition of N-(9-fluorenylmethoxycarbonyloxy)succinimide to a slurry of the primary amine in methanol-dimethylformamide under anhydrous conditions in the presence of a base such as pyridine.

Intermediate compounds of formula (II) are novel compounds and as such form part of the invention.

Certain intermediate compounds derived from amphotericin B by steps (a) to (c) as hereinbefore described, which are themselves precursors to compounds of formula (II), are novel compounds and as such form part of the invention.

If required, compounds of formula (I) in which $R_2$ is hydrogen and/or $R_3$ is hydrogen may be converted to compounds of formula (I) in which $R_2$ is $C_{1-8}$ alkyl and/or $R_3$ is an amine protecting group using steps (b) and (c) hereinbefore described for the preparation of intermediate compounds of formula (II).

The compounds of the formula (I) and their pharmaceutically acceptable salts are anti-fungal agents, potentially useful in combating fungal infections in animals, including humans. For example they are potentially useful in treating topical fungal infections in man caused by, among other organisms, species of *Candida, Trichophyton, Microsporum* or *Epidermophyton*, or in mucosal infections caused by *Candida albicans* (e.g. thrush and vaginal candidiasis). They may also be used in the treatment of systemic fungal infections caused by, for example *Candida albicans, Cryptococcus neoformans, Aspergillus fumigatus, Coccidioides, Paracoccidioides, Histoplasma* or *Blastomyces* spp. They may also be of use in treating eumycotic mycetoma, chromoblastomycosis, and phycomycosis.

The invention further provides a pharmaceutical composition comprising a compound of the formula (I) or a pharmaceutically acceptable salt thereof together with a pharmaceutically acceptable diluent or carrier. The composition is preferably for human use in tablet, capsule, injectable or cream form.

For human use, the antifungal compounds of the formula (I) or pharmaceutically acceptable salts thereof can be administered alone, but will generally be administered in admixture with a pharmaceutical carrier selected with regard to the intended route of administration and standard pharmaceutical practice. For example, they may be administered orally in the form of a tablet containing such excipients as starch or lactose, or in a capsule or ovule either alone or in admixture with excipients, or in the form of an elixir or suspension containing a flavouring or colouring agent. They may be injected parenterally, for example, intravenously, intramuscularly or subcutaneously. For parenteral administration, they are best used in the form of a sterile aqueous solution which may contain other substances, for example, enough salts or glucose to make the solution isotonic.

For oral and parenteral administration to human patients, it is expected that the daily dosage level of the antifungal compounds of the formula (I) will be from 0.1 to 1 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

Within the indicated dose range, no adverse toxicological effects have been observed with the compounds of the invention which would preclude their administration to suitable patients for the treatment of fungal infections.

The present invention further provides a compound of formula (I) or a pharmaceutically acceptable salt thereof for use as an active therapeutic substance.

A compound for use as an active therapeutic substance is intended for use in the treatment of disorders in animals including humans. As stated above, compounds of formula (I) and their pharmaceutically acceptable salts have anti-fungal activity and are potentially useful in combating fungal infections in animals including humans.

Accordingly the present invention further provides a compound of formula (I) or a pharmaceutically acceptable salt thereof for use in the treatment of fungal infections.

The present invention additionally provides a method of treatment of fungal infections in animals., including humans, which comprises administering an effective anti-fungal amount of a compound of formula (I) or a pharmaceutically acceptable salt thereof to the animal.

The present invention also provides the use of a compound of formula (I) or a pharmaceutically acceptable salt thereof for the manufacture of a medicament for use as an active therapeutic substance in the treatment of fungal infections in animals, including humans.

The following Examples illustrate the preparation of compounds of the invention and the following Descriptions illustrate the preparation of novel intermediates thereto.

DESCRIPTION 1

N-Acetyl-13-O-methylamphotericin B methyl ester (D1)

give the title compound (D1) which was used without further purification.

[1] Nicolaou et al., J. American Chem. Soc., 110, 4660, (1988).

DESCRIPTION 2

N-(9-Fluorenylmethoxycarbonyl)amphotericin B (D2)

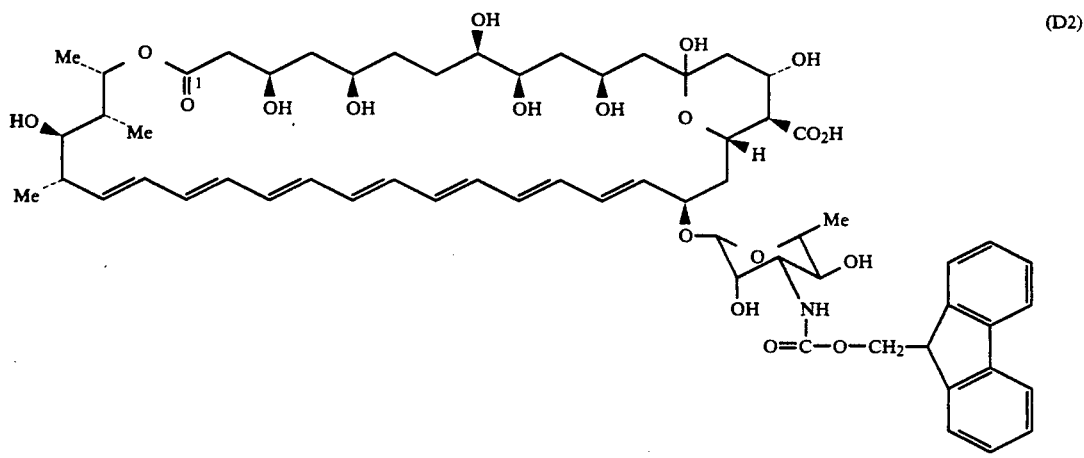

To a solution of amphotericin B (0.50 g, 0.54 mmol) and anhydrous potassium carbonate (0.17 g, 1.2 mmol) in dry dimethylsulphoxide (10 ml) and dry methanol (2 ml) under a nitrogen atmosphere at 0° C., was added solid 9-fluorenylmethyl chloroformate (0.21 g, 0.81 mmol). After stirring for 1 hour a further portion of 9-fluorenylmethyl chloroformate (0.04 g, 0.17 mmol) was added. After 0.25 hours the reaction mixture was poured into distilled water (200 ml). The precipitate was collected by centrifugation, dissolved in methanol and evapo-

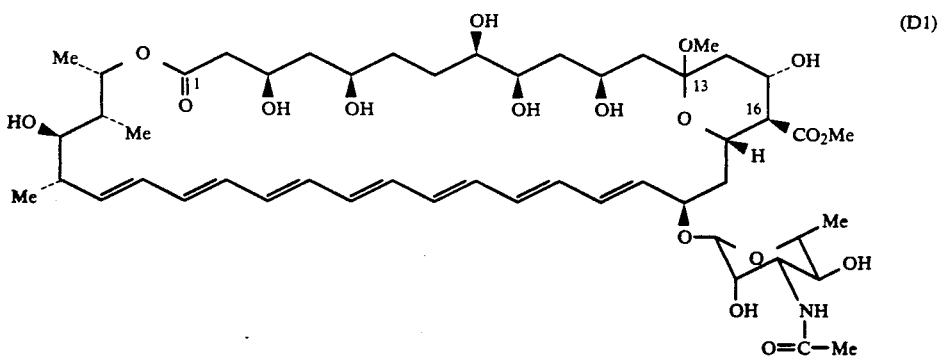

N-Acetylamphotericin B methyl ester[1] (0.30 g, 0.31 mmol) was dissolved in dry methanol (14 ml) and dry tetrahydrofuran (3 ml) under a nitrogen atmosphere. Anhydrous 10-camphorsulphonic acid (0.03 g, 0.13 mmol) was added and the solution was stirred for 0.5 hours. Dry triethylamine (0.02 ml, 0.15 mmol) was added and the solution was concentrated in vacuo. The concentrated solution was poured into sodium dried diethyl ether (400 ml) and the precipitate was filtered and washed with sodium dried diethyl ether (100 ml) to rated in vacuo. The residue was dissolved in the minimum volume of a mixture of tetrahydrofuran and methanol (1:1) and poured into distilled water (200 ml, adjusted to pH 3.2 by the addition of glacial acetic acid). The preciptate was centrifuged, washed with water and dried in vacuo to give the title compound (D2) which was used without further purification.

DESCRIPTION 3

N-(9-Fluorenylmethoxycarbonyl)amphotericin B methyl ester (D3)

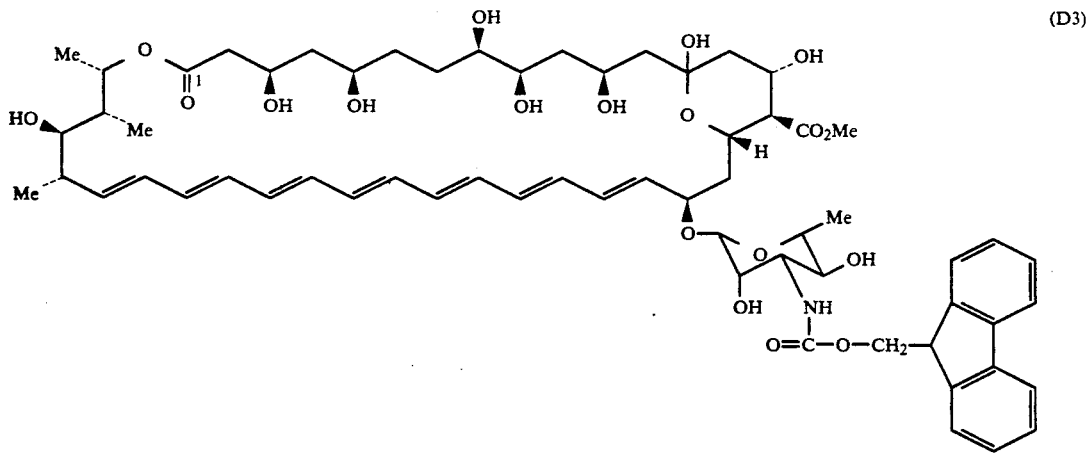

Crude N-(9-fluorenylmethoxycarbonyl)amphotericin B (D2) (0.36 g, 0.31 mmol) was dissolved in 1:1 dimethylsulphoxide and methanol (20 ml). At 0° C. and with stirring, a solution of diazomethane in diethyl ether (25 ml) was added over 0.3 hours. The diazomethane was generated from; Diazald ® (0.39 g, 1.8 mmol); potassium hydroxide (0.18 g, 3.2 mmol); water (1 ml) and 2-(2-ethoxyethoxy)ethanol (2 ml). The reaction was stirred for a further 1.5 hours and then quenched cautiously with glacial acetic acid. The product was precipitated by pouring into diethyl ether. It was collected by centrifugation, washed with diethyl ether, dissolved in methanol and evaporated in vacuo.

The crude material was purified by means of medium pressure column chromatography on silica-gel eluting with ethyl acetate/methanol mixtures. The title compound (D3) was obtained as a yellow solid. $\delta_H 270$ MHz[$d_8$THF/$d_4$-MeOH] 7.78 (2H,d,J 6.9 Hz), 7.70 (2H,d,J 7.4 Hz), 7.35 (2H,dd,J 7.4 and 6.3 Hz), 7.28 (2H,t,7.4 Hz), 6.63–5.93 (13H, complex), 5.50 (1H,m), 5.32 (1H,dd,J 10.2 and 14.8 Hz), 4.75–4.04 (10 H, complex), 3.90–3.0 (8H, complex), 3.74 (3H,s) 2.50–1.15 (19H, complex), 1.28 (3H,d,J 6.2 Hz), 1.20 (3H,d,J 6.3 Hz), 1.10 (3H,d,J 6.3 Hz) and 0.99 (3H,d,J 7.2 Hz)ppm.

Hplc: Reverse phase using: ODS 5µ 250×4.6 mm column; eluant 80% methanol—20% pH 3 phosphate buffer—1 ml/min; detection wavelength 350 nm; Retention time 18.8 minutes.

DESCRIPTION 4

N-(9-Fluorenylmethoxycarbonyl)amphotericin B (D4)

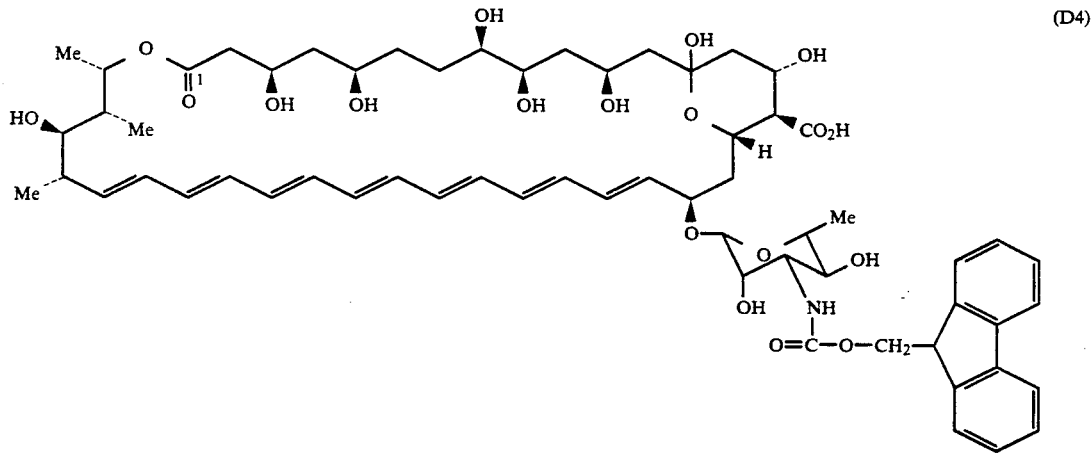

To a slurry of amphotericin B (4.00 g, 4.33 mmol) in dry dimethylformamide (240 ml), dry methanol (80 ml) and dry pyridine (0.42 ml, 5.19 mmol) was added solid N-(9-fluorenylmethoxycarbonyloxy) succinimide (2.36 g, 7.00 mmol). The reaction was stirred for 2 hours, diluted with methanol (160 ml) and poured into distilled water (7 liters) at pH 4 (acetic acid). The precipitate was filtered, washed with water and dried in vacuo to give the title compound (D4) which was used without further purification.

DESCRIPTION 5

N-(9-Fluorenylmethoxycarbonyl)amphotericin B methyl ester (D5)

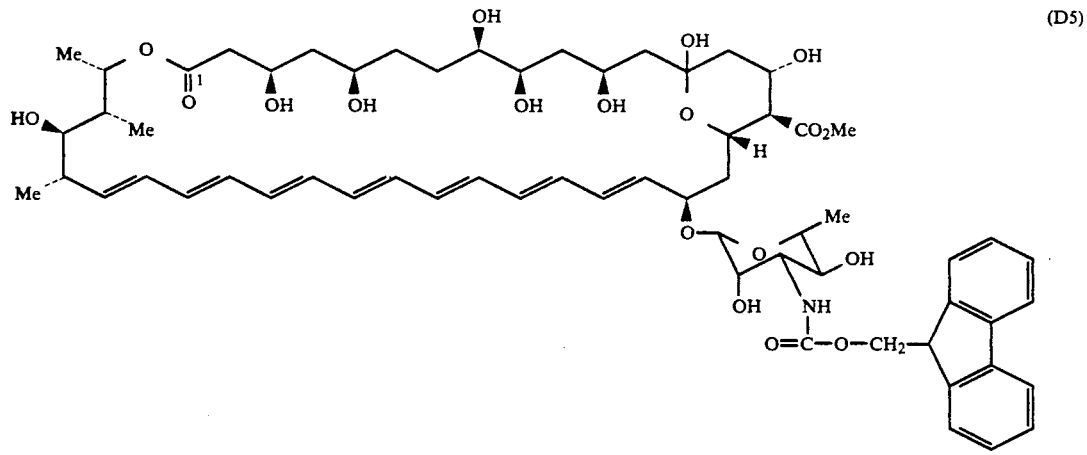

Crude N-(9-fluorenylmethoxycarbonyl)amphotericin B (D4) (2.11 g, 1.84 mmol) was dissolved in 1:1 dimethylsulphoxide and methanol (27 ml). At 0° C. and with stirring, a solution of diazomethane in diethyl ether (13 ml) was added over 0.3 hours. The diazomethane was generated from; Diazald ® (1.97 g, 9.20 mmol); potassium hydroxide (0.56 g, 10.00 mmol); water (1 ml) and 2-(2-ethoxyethoxy)ethanol (3.3 ml). The reaction was stirred for a further 0.5 hours and then quenched cautiously with glacial acetic acid. The product was precipitated by pouring into diethyl ether (4 liters), filtered, washed with diethyl ether and dried in vacuo giving a yellow solid.

Hplc: Reverse phase using: ODS 5μ 250×4.6 mm column; eluant 80% methanol −20% pH3 phosphate buffer—1 ml/min; detection wavelength 350 nm; retention time 18.8 minutes.

N-(9-Fluorenylmethoxycarbonyl)amphotericin B methyl ester prepared according to Description 3 or Description 5 (7.38 g, $6.36 \times 10^{-3}$ mol) suspended in a 4:1 mixture of dry methanol/tetrahydrofuran (400 ml) was treated with 10-camphorsulphonic acid (1.42 g, $5.66 \times 10^{-3}$ mol), to lower the pH of the reaction mixture to ca. 2.5. After 1.2 h the reaction mixture was neutralised with triethylamine (700 μl, $5.02 \times 10^{-3}$ mol), concentrated and poured into diethyl ether (10 liters). The yellow product, N-(9-fluorenylmethoxycarbonyl)-13-O-methylamphotericin B methyl ester (D6) was filtered, washed with diethyl ether and dried under vacuum.

Hplc: Reverse phase ODS 5μ 250×4.6 mm column; eluant 78% methanol-22% pH 3 phosphate buffer—1 mlmin$^{-1}$; detection wavelength 350 nm; Retention time: 12.7 minutes. Mass spectrum FAB (thioglycerol matrix) observed mass 1196—calculated mass for $C_{64}H_{87}NO_{19}Na = 1196.6$.

DESCRIPTION 6

N-(9-Fluorenylmethoxycarbonyl)-13-O-methylamphotericin B methyl ester (D6)

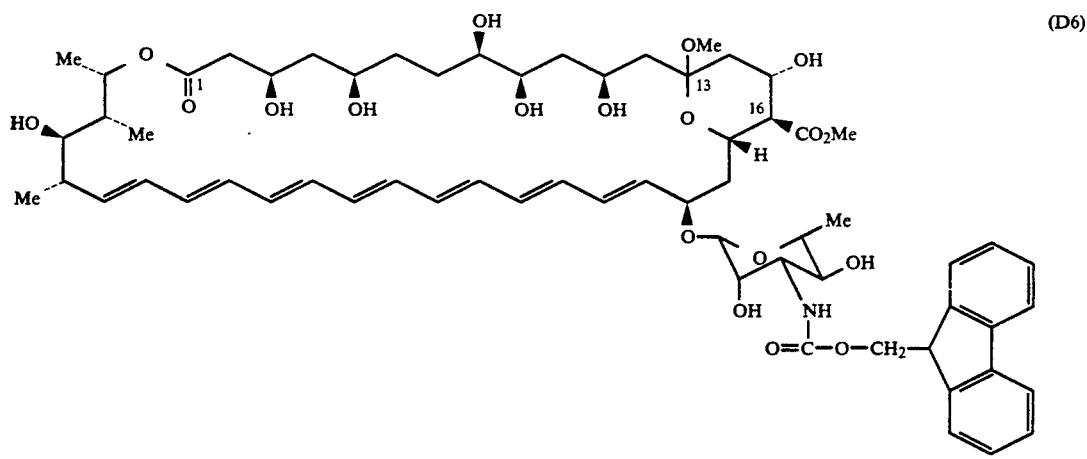

EXAMPLE 1

N-Acetyl-16-decarboxy-16-hydroxymethyl-13-O-methylamphotericin B (E1)

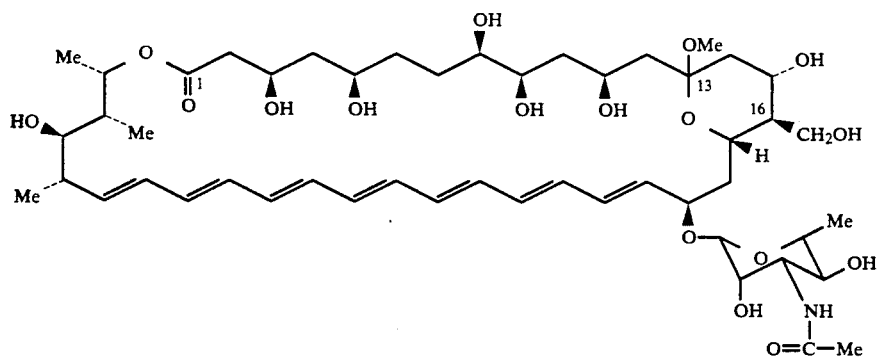

(E1)

Crude N-acetyl-O-methylamphotericin B methyl ester (D1) (0.24 g, 0.24 mmol) was dissolved in dry methanol (6 ml) and dry tetrahydrofuran (2 ml) and solid sodium borohydride (0.23 g, 6.19 mmol) was added portionwise. The solution was stirred for 0.75 hours, then concentrated and poured into saturated sodium bicarbonate solution (250 ml). The aqueous solution was extracted with ethyl acetate and methanol mixtures. The combined organic phases were evaporated in vacuo. The crude material thus obtained was purified by means of medium pressure column chromatography on silica-gel eluting with the lower phase of chloroform, methanol and concentrated ammonia solution (5:2:2). The title compound (E1) was obtained as a yellow solid. $\delta_H 270 MHz[(CD_3)_2SO]$ 7.66 (1H,d,J 8.0 Hz), 6.60–6.00 (12H, complex), 5.89 (1H,dd,J 7.4 and 15.5 Hz), 5.57 (1H,dd,J 8.1 and 13.5 Hz), 5.01(1H,m), 4.85–4.15 (14H, complex), 4.10–3.15 (12H, complex), 2.99 (3H,s) 2.40–2.05 (4H, complex), 1.85 (3H,s), 1.83–1.60 (3H, complex), 1.58–1.30 (12H, complex), 1.18 (3H,d,J 6.1 Hz), 1.15 (3H,d,J 6.9 Hz), 1.07 (3H,d,J 6.2 Hz) and 0.91 (3H,d,J 7.2 Hz)ppm.

Mass Spectrum: FAB (Thioglycerol Matrix) observed masses 988 and 965 calculated mass for $C_{50}H_{79}NO_{17}Na$ 988 and calculated mass for $C_{50}H_{79}NO_{17}$ 965.

Hplc: Reverse phase using: ODS 5μ 250×4.6 mm column; eluant 75% Methanol—25% pH 3 phosphate buffer—1 ml/min, detection wavelength 350 nm; Retention time 6.2 minutes.

EXAMPLE 2

N-(9-Fluorenylmethoxycarbonyl)-16-decarboxy-16-hydroxymethyl-13-O-methyl amphotericin B (E2)

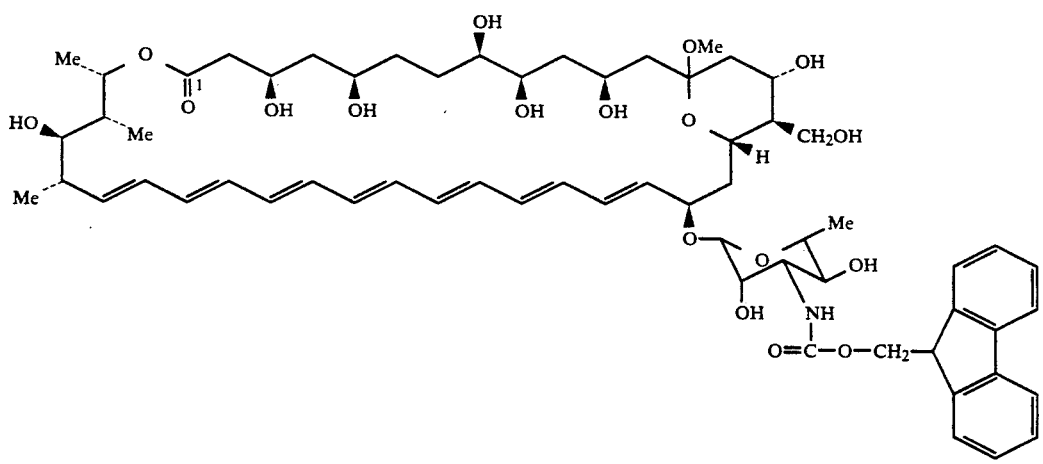

(E2)

N-(9-Fluorenylmethoxycarbonyl)-13-O-methylamphotericin B methyl ester (D6) (6.75 g, 5.75×10$^{-3}$ mol), dissolved in a 3:1 mixture of methanol/tetrahydrofuran (185 ml), was treated with sodium borohydride (5.65 g, 1.50×10$^{-1}$ mol) at 0° C. After addition of the sodium borohydride the reaction mixture was allowed to reach ambient temperature. After 30 minutes saturated sodium hydrogen carbonate solution (3 ml) was added to the reaction mixture. The mixture was concentrated and poured into saturated sodium hydrogen carbonate solution (8 liters). The yellow product, N-(9-fluorenylmethoxycarbonyl)-16-decarboxy-16-hydroxymethyl-13-O-methylamphotericin B was filtered, washed with water and dried under vacuum.

The crude material was purified by means of column chromatography on normal phase silica-gel eluting with dichloromethane and methanol mixtures to give the title compound (E2).

vmax (KBr disc) 3415, 3010, 2925, 1710, 1510, 1445, 1375, 1320, 1180, 1065, 1005, 900, 845, 760 and 740 cm$^{-1}$. δH400MHz [($C_5D_5N:CD_3OD$;1:1)] 7.85 (2H,d,J 7.6 Hz), 7.72 (1H,d,J 7.9 Hz), 7.70 (1H,d,J 7.9 Hz), 7.43 (1H,d,J 7.4 Hz), 7.41 (1H,d,J 7.5 Hz), 7.30 (2H,dd,J 6.4 and 7.2 Hz), 6.60–6.26 (12H, complex), 6.13 (1H,dd,J 14.7 and 7.6 Hz), 5.59 (1H,m), 5.52 (1H,m), 4.93 (1H,s), 4.82 (1H,m), 4.48 (1H,m), 4.44–4.31 (1H,m), 4.39 (2H,d,J 7.3 Hz), 4.29–4.16 (5H,m), 4.08 (2H,m), 3.98

(1H,m), 3.83 (1H,m), 3.78 (1H,dd,J 9.5 and 9.9 Hz), 3.59 (1H,m), 3.51 (1H,m), 3.48–3.42 (1H,m), 3.24 (3H,s), 2.65–2.35 (5H,m, [including 1H,dd,J 16.7 and 9.2 Hz]), 2.20 (1H,m), 2.10–1.41 (13H, complex), 1.48 (3H,d,J 6.1 Hz), 1.35 (3H,d,J 6.4 Hz), 1.25 (3H,d,J 6.5 Hz) and 1.16 (3H,d,J 7.1 Hz) ppm.

Mass spectrum FAB (3-NOBA sodium matrix) observed mass 1168—calculated mass for $C_{63}H_{87}NO_{18}\cdot Na = 1168.6$.

Hplc: Reverse phase ODS 5μ 250×4.6 mm column; eluant 78% methanol—22% pH 3 phosphate buffer—1 mlmin$^{-1}$; detection wavelength 350 nm; Retention time: 11.0 minutes.

EXAMPLE 3

N-(9-Fluorenylmethoxycarbonyl)-16-decarboxy-16-hydroxymethylamphotericin B (E3)

$\nu$max (KBr disc) 3408, 3014, 2932, 1709, 1637, 1516, 1451, 1379, 1188, 1070, 1012, 904, 783, 761 and 742 cm$^{-1}$.

δ6400 MHz [($C_5D_5N:CD_3OD$; MIN:MAJ)], 7.84 (2H,d,J 7.7 Hz), 7.72 (1H,d,J 7.8 Hz), 7.70 (1H,d,J 7.8 Hz), 7.42 (1H,d,J 7.4 Hz), 7.40 (1H,d,J 7.5 Hz), 7.31 (1H,d,J 7.2 Hz), 7.29 (1H,d,J 7.3 Hz), 6.67–6.17 (13H, complex), 5.59 (1H,m), 5.48 (1H,dd,J 14.4 and 10.2 Hz), 4.90 (1H,s), 4.68 (1H,m), 4.65–4.55 (2H,m), 4.45–4.30 (2H,m), 4.35 (2H,d,J 7.3 Hz), 4.21 (1H,t,J 7.0 Hz), 4.18 (1H,d,J 3.0 Hz), 4.15–3.95 (3H,m), 3.91 (1H,m), 3.82 (1H,m), 3.69 (1H,dd,J 9.7 and 9.7 Hz), 3.59–3.48 (1H,m), 3.41–3.31 (2H,m), 2.67 (1H,m), 2.60–2.49 (1H,m), 2.45 (1H,dd,J 16.8 Hz and 9.7 Hz), 2.32 (1H,dd,J 16.8 and 2.6 Hz), 2.26 (1H,m), 2.15–1.38 (14H, complex), 1.44 (3H,d,J 6.3 Hz), 1.33 (3H,d,J 6.4 Hz), 1.22 (3H,d,J 6.4 Hz) and 1.15 (3H,d,J 7.5 Hz) ppm. Mass spectrum FAB

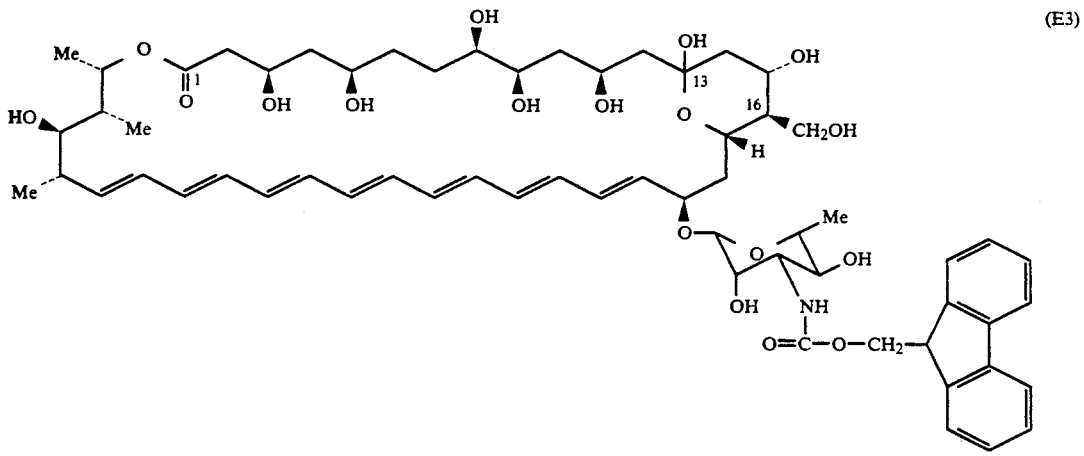

(E3)

N-(9-Fluorenylmethoxycarbonyl)-16-decarboxy-16-hydroxymethyl-13-O-methylamphotericin B (E2) (0.85 g, 7.37×10$^{-4}$ mol) suspended in a 2:1 mixture of tetrahydrofuran/water (80 ml) was treated with 10-camphorsulphonic acid (0.56 g, 2.24×10$^{-3}$ mol) (lowering the pH of the reaction mixture to ca. 2.5). After 0.5 h the reaction mixture was neutralised with triethylamine (80 μl, 5.74×10$^{-4}$ moles), concentrated and poured into water (2 liters). The yellow product was centrifuged out, washed with water and dried under vacuum.

The crude material was purified by means of column chromatography on reverse phase silica-gel eluting with tetrahydrofuran and water mixtures. The purified product (E3) was isolated after concentration in vacuo and freeze drying.

(3-NOBA sodium matrix) observed mass 1154—calculated mass for $C_{62}H_{85}NO_{18}Na = 1154.5$.

Hplc: Reverse phase ODS 5μ 250×4.6 mm column; eluant 80% methanol—20% pH 3 phosphate buffer —1 mlmin$^{-1}$; detection wavelength 350 nm; Retention time:13.2 minutes.

EXAMPLE 4

16-Decarboxy-16-hydroxymethylamohotericin B (E4)

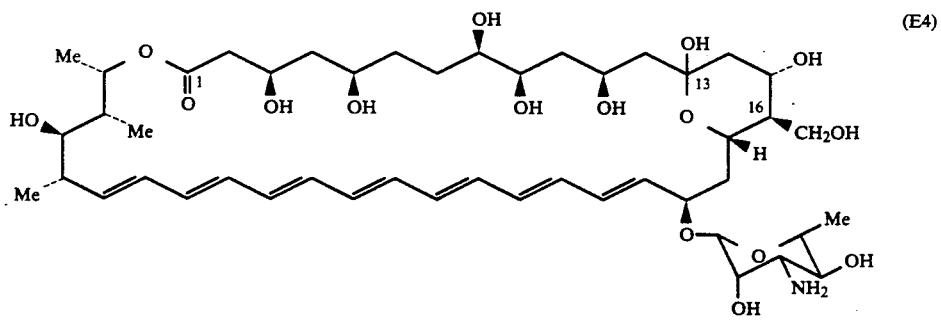

N-(9-Fluorenylmethoxycarbonyl)-16-decarboxy-16-hydroxymethylamphotericin B (E3) (0.35 g, 3.01×10$^4$ mol) dissolved in a 3.5:1 mixture of dimethyl sulphoxide/methanol (4 ml) was treated with piperidine (58 μl, 5.89×10$^{-4}$ mol). After 3 hours the reaction product was precipitated as a yellow solid from diethyl ether (2 liters). The product was collected by filtration, washed with diethyl ether and dried under vacuum.

The crude material was purified by means of column chromatography on reverse phase silica-gel eluting with tetrahydrofuran and water mixtures. The purified product (E4) was isolated after concentration in vacuo and freeze drying. $\nu$max (KBr disc) 3380, 3005, 2910, 1710, 1630, 1440, 1375, 1320, 1180, 1070, 1010, 880, 845 and 790 cm$^{-1}$. $\delta$H 400 MHz [($C_5D_5N:CD_3OD$; 1:1)], 6.70–6.25 (13H, complex), 5.64 (1H,m), 5.51 (1H,dd,J 14.6 and 10.2 Hz), 5.02 (1H,s), 4.77 (1H,m), 4.70–4.61 (2H,m), 4.50–4.33 (2H,m), 4.41 (1H,d,J 2.7 Hz), 4.15 (1H,dd,J 11.1 and 3.8 Hz), 4.08 (1H,dd,J 11.1 and 3.4 Hz), 3.96 (1H,m), 3.87 (1H,m), 3.79 (1H,dd,J 9.6 and 9.6 Hz), 3.59 (1H,m), 3.49–3.33 (3H,m), 2.75 (1H,m), 2.63–2.53 (1H,m), 2.49 (1H,dd,J 16.8 and 9.7 Hz), 2.35 (1H,dd,J 16.8 and 2.5 Hz), 2.32 (1H,m), 2.20–1.38 (14H, complex), 1.46 (3H,d,J 6.1 Hz), 1.36 (3H,d,J 6.4 Hz), 1.25 (3H,d,J 6.4 Hz) and 1.17 (3H,d,J 7.1 Hz) ppm.

Mass spectrum FAB (3-NOBA sodium matrix) observed mass 932—calculated mass for $C_{47}H_{75}NO_{16}Na = 932.5$.

Hplc: Reverse phase ODS 5$\mu$ 250×4.6 mm column; eluant 80% methanol—20% pH 3 phosphate buffer—1 mlmin$^{-1}$; detection wavelength 350 nm; Retention time: 9.6 minutes.

UV-vis (CH$_3$OH) $\lambda$max 408 (E$_{1cm}^{1\%}$ 1461), 384 (1310), 364 (796) and 345 nm (377).

EXAMPLE 5

16-Decarboxy-16-hydroxymethyl-13-O-methyl amphotericin B (E5)

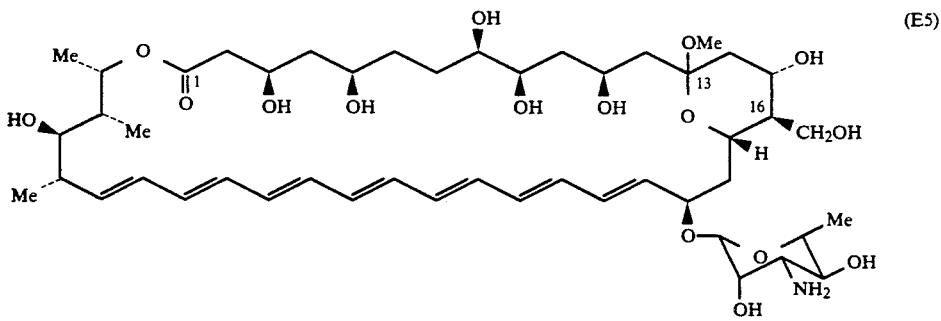

(E5)

The compound of Example 2 (146 mg, 0.13 mmol) dissolved in a 3.5:1 mixture of dimethyl sulphoxide/methanol (3 ml) was treated with piperidine (25 $\mu$l, 0.25 mmol). After 1.25 hours the reaction mixture was poured into diethyl ether (0.4 L) and the precipitated solid filtered and washed with diethyl ether. The crude material was purified by flash chromatography on silica-gel eluting with the lower phase of chloroform:methanol: 0.880 ammonia mixtures to give the title compound as a yellow solid.

$\delta$H400 MHz (d$_4$-methanol/d$_5$-pyridine): 6.60–6.25 (12H, series of m), 6.10 (1H, dd, J 14.7 and 7.5 Hz), 5.57 (1H, dd, J 14.4 and 9.6 Hz), 5.49 (1H, m), 4.85 (1H, s), 4.80 (1H, m), 4.44 (1H, m), 4.30 (1H, dt, J 10.6 and 4.7 Hz), 4.20–4.10 (3H, m), 4.12 (1H, d, J 2.9 Hz), 4.03 (1H, dd, J 11.0 and 3.3 Hz), 3.95 (1H, m), 3.80 (1H, m), 3.52–3.35 (4H, m), 3.23 (3H, s), 2.81 (1H, dd, J 9.2 and 2.9 Hz), 2.60–2.35 (5H, m, including at 2.49 (1H, dd, J 16.7 and 9.1 Hz)), 2.17 (1H, m), 2.06–1.87 (4H, m), 1.85–1.52 (9H, series of m), 1.42 (3H, d, J 5.6 Hz), 1.33 (3H, d, J 6.4 Hz), 1.23 (3H, d, J 6.4 Hz), 1.14 (3H, d, J 7.1 Hz) ppm.

Mass spectrum: FAB (3-NOBA/sodium matrix) observed mass 946—calculated mass for $C_{48}H_{77}NO_{16}Na^+ = 946.5$.

HPLC: Reverse phase ODS 5$\mu$ 250×4.6 mm column; eluent 76% methanol—24% pH 3.5 phosphate buffer—1 mlmin$^{-1}$; detection wavelength 350 nm; retention time: 8.6 minutes.

MIC Data

Method

The Minimum Inhibitory Concentration (MIC) was determined by diluting the test compound in a broth medium in a microtitre tray. The organisms, which had been grown previously in a broth medium, were diluted and added to the wells to provide a final inoculum of approximately 10$^5$ colony-forming units per well. The trays were incubated at 37° C. and the turbidity of each well noted at intervals. The MIC was taken as the lowest concentration (in $\mu$g/ml) which prevented significant growth.

Results

| Minimum Inhibitory Concentration ($\mu$g/ml) (determined after 2 and 3 days incubation) | | | |
|---|---|---|---|
| | | EXAMPLE 4 | |
| ORGANISM* | DAY | YNB | SAB |
| Candida albicans | 2 | 1 | 1 |
| 73/079 | 3 | 2 | 1 |
| Candida | 2 | 8 | 1 |
| parapsilosis | 3 | 8 | 2 |
| 937 A | | | |

*Inoculum 10$^5$ cells/ml
YNB: Yeast Nitrogen Base Broth
SAB: Sabouraud's Dextrose Broth.

What is claimed is:

1. A compound of formula (I), or a pharmaceutically acceptable salt thereof:

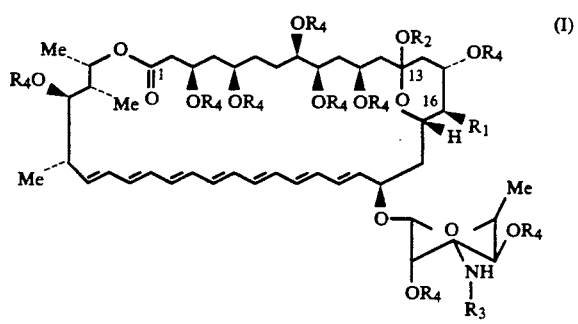

(I)

wherein R$_1$ is —CH$_2$OH; R$_2$ is hydrogen or C$_{1-8}$ alkyl; R$_3$ is hydrogen or an amine protection group selected from the group consisting of acetyl, 9-fluorenylmethoxycarbonyl, trichloroethoxycarbonyl, 2-methylsulphonylethoxycarbonyl, and 2-trimethylsilylethoxycarbonyl; and each $R_4$ is hydrogen.

2. A compound according to claim 1 wherein $R_2$ is hydrogen or methyl.

3. A compound according to claim 1 wherein $R_2$ is hydrogen or methyl and $R_3$ is hydrogen, acetyl or 9-fluorenylmethoxycarbonyl.

4. A compound selected from the group consisting of:
N-acetyl-16-decarboxy-16-hydroxymethyl-13-O-methylamphotericin B;
N-(9-fluorenylmethoxycarbonyl)-16-decarboxy-16-hydroxymethyl-13-O-methyl amphotericin B;
N-(9-fluorenylmethoxycarbonyl)-16-decarboxy-16-hydroxymethylamphotericin B;
16-decarboxy-16-hydroxymethylamphotericin B; and
16-decarboxy-16-hydroxymethyl-13-O-methylamphotericin B.

5. A pharmaceutical composition comprising a pharmaceutically effective amount of a compound of formula (I) or a pharmaceutically acceptable salt thereof, as defined in claim 1, together with a pharmaceutically acceptable diluent or carrier.

6. A method of treatment of fungal infections in animals, which comprises administering an effective antifungal amount of a compound of formula (I) or a pharmaceutically acceptable salt thereof, as defined in claim 1, to an animal in need of such treatment.

* * * * *